(12) United States Patent
Maurer et al.

(10) Patent No.: US 6,403,600 B1
(45) Date of Patent: Jun. 11, 2002

(54) METHOXIMINOPHENYLACETIC ACID AMIDES

(75) Inventors: Fritz Maurer, Leverkusen; Herbert Gayer, Monheim; Peter Gerdes, Aachen; Ulrich Heinemann, Leichlingen; Bernd-Wieland Krüger, Bergisch Gladbach; Robert Markert, Köln; Klaus Stenzel, Düsseldorf; Gerd Hänssler, Leverkusen; Astrid Mauler-Machnik, Leichlingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/762,840

(22) PCT Filed: Aug. 4, 1999

(86) PCT No.: PCT/EP99/05643

§ 371 (c)(1),
(2), (4) Date: Apr. 5, 2001

(87) PCT Pub. No.: WO00/10970

PCT Pub. Date: Mar. 2, 2000

(30) Foreign Application Priority Data

Aug. 17, 1998 (DE) .......................................... 198 37 065
Jun. 5, 1999 (DE) .......................................... 199 25 780

(51) Int. Cl.$^7$ ..................... C07C 313/28; C07C 275/40; C07C 251/48; C07F 9/24; A01N 37/28
(52) U.S. Cl. ........................ 514/269; 546/102; 544/319; 514/608
(58) Field of Search .......................... 564/102; 514/269, 514/608; 544/319

(56) References Cited

U.S. PATENT DOCUMENTS

| | | | |
|---|---|---|---|
| 5,185,342 A | 2/1993 | Hayase et al. | 514/274 |
| 5,248,687 A | 9/1993 | Hayase et al. | 514/346 |
| 5,360,810 A | 11/1994 | Hayase et al. | 514/346 |
| 5,371,223 A | 12/1994 | Hayase et al. | 544/316 |
| 5,401,877 A | 3/1995 | Hayase et al. | 564/147 |
| 5,548,078 A | 8/1996 | Hayase et al. | 544/298 |

FOREIGN PATENT DOCUMENTS

WO  97/00856  1/1997

*Primary Examiner*—Mukund J. Shah
*Assistant Examiner*—Hong Liu
(74) *Attorney, Agent, or Firm*—Joseph C. Gil; Raymond J. Harmuth

(57) ABSTRACT

The invention relates to novel methoximinophenylacetamides, to a process for their preparation and to their use as fungicides.

14 Claims, No Drawings

METHOXIMINOPHENYLACETIC ACID AMIDES

The invention relates to novel methoximinophenylacetamides, to a process for their preparation and to their use as fungicides.

It is already known that certain compounds which are constitutionally similar to those described below have fungicidal properties (compare, for example, EP-A-398 692, EP-A-528 681, WO 97/00 856). However, the fungicidal activity of these compounds is unsatisfactory, in particular at low application rates.

This invention, accordingly, provides the novel methoximinophenylacetamides of the general formula (I)

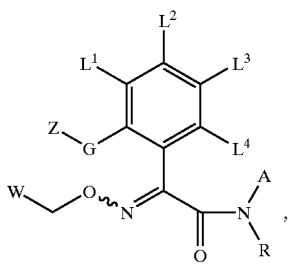

(I)

in which
A represents hydrogen, alkoxycarbonyl, methyl, ethyl or cyclopropyl, or has the same meaning as R,
R represents alkylthio, halogenoalkylthio, optionally substituted arylthio, alkoxycarbonylthio, alkylthiocarbonyl, —S—Y, —S—N($R^1R^2$), —CO—N($R^3R^4$), —CN, —$CH_2$—O—$R^5$, —PO(O$R^6$)$R^7$, —PS(O$R^6$)$R^7$, in which
$R^1$ represents alkyl,
$R^2$ represents alkyl, alkoxycarbonyl, or together with $R^1$ and the nitrogen atom to which they are attached represents an optionally substituted heterocyclic ring,
$R^3$ represents alkyl or optionally substituted aryl,
$R^4$ represents alkylthio, alkylsulphonyl or halogenoalkylthio, or together with $R^3$ and the nitrogen atom to which they are attached represents an optionally substituted heterocyclic ring,
$R^5$ represents alkyl,
$R^6$ represents alkyl,
$R^7$ represents alkyl, alkoxy or alkylamino,
Y represents the same grouping which is already linked to the S atom,
or, if A represents methyl,
R also represents alkylcarbonyl, alkoxycarbonyl, halogenoalkoxycarbonyl, alkoxycarbonylcarbonyl, alkylaminocarbonyl, dialkylaminocarbonyl, alkylsulphonyl or optionally substituted arylsulphonyl,
G represents a single bond, represents oxygen, sulphur or represents in each case optionally halogen-, hydroxyl-, alkyl-, halogenoalkyl- or cycloalkyl-substituted alkanediyl, alkenediyl, alkinediyl or one of the groupings below, in which in each case the left side is attached to Z: —Q—CQ—, —CQ—Q—, —$CH_2$—Q—; —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$^n$—$CH_2$—, —C($R^8$)=N—O—, —C($R^8$)=N—O—$CH_2$—, —N($R^9$)—, —CQ—N($R^9$)—, —N($R^9$)—CQ—, —Q—CQ—N($R^9$)—, —N=C($R^8$)—Q—$CH_2$—, —CH($R^8$)—O—N=CH—, —C($R^8$)=N—N=CH—, —N($R^9$)—CQ—Q—, —CQ—N($R^9$)—CQ—Q—, —N($R^9$)—CQ—Q—$CH_2$—, —Q—C($R^8$)=N—O—$CH_2$—, —N($R^9$)—C($R^8$)=N—O—$CH_2$—, —O—$CH_2$—C($R^8$)=N—O—$CH_2$—, —N=N—C($R^8$)=N—O—$CH_2$—, —C(=N—O—$R^{10}$)—C($R^8$)=N—O—$CH_2$—, —C(=N—O—$R^{10}$)—C($R^8$)—O—N=CH—, —C(=N—O—$R^{10}$)—C($R^8$)=N—N=CH—, —C(=N—O—$R^{10}$)—C($R^8$)—O—N=C(CH$_3$)—, —T—Ar$^1$—or—T—Ar$^1$—Q—, where
Ar$^1$ represents optionally substituted arylene, heteroarylene, cycloalkylene or heterocycloalkylene (i.e. a doubly attached aliphatic ring in which one or more carbon atoms are replaced by heteroatoms, i.e. atoms different from carbon),
n represents the number 0, 1 or 2,
Q represents oxygen or sulphur,
$R^8$ represents hydrogen, cyano or in each case optionally substituted alkyl, alkoxy, alkylthio, alkylamino, dialkylamino or cycloalkyl,
$R^9$ represents hydrogen, hydroxyl, cyano or in each case optionally substituted alkyl, alkoxy or cycloalkyl,
$R^{10}$ represents hydrogen, alkyl or optionally substituted benzyl and
T represents a single bond, represents oxygen, sulphur, —$CH_2$—O—, —$CH_2$—S— or represents optionally substituted alkanediyl,
$L^1$, $L^2$, $L^3$ and $L^4$ are identical or different and independently of one another each represent hydrogen, halogen or alkyl,
W represents hydrogen, fluorine, cyano or thiocyanato and
Z represents in each case optionally substituted alkyl, alkenyl, alkinyl, cycloalkyl, aryl or heterocyclyl.

In the definitions, the saturated or unsaturated hydrocarbon chains, such as alkyl, are in each case straight-chain or branched, including in combination with heteroatoms, such as in alkoxy or alkylthio.

Halogenoalkyl represents partially or fully halogenated alkyl. In the case of polyhalogenated halogenoalkyl, the halogen atoms can be identical or different. Preferred halogen atoms are fluorine and chlorine and in particular fluorine. If the halogenoalkyl carries further substituents, the maximum possible number of the halogen atoms is reduced to the remaining free valencies.

Halogen generally represents fluorine, chlorine, bromine or iodine, preferably fluorine, chlorine or bromine, in particular fluorine or chlorine.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen and sulphur. If the ring contains a plurality of oxygen atoms, these are not directly adjacent. If appropriate, the cyclic compounds form, together with other carbocyclic or heterocyclic, fused-on or bridged rings, a polycyclic ring system. A polycyclic ring system can be attached via the heterocyclic ring or a fused-on carbocyclic ring. Preference is given to mono- or bicyclic ring systems, in particular to mono—or bicyclic aromatic ring systems.

Furthermore, it has been found that the novel methoximinophenylacetamides of the general formula (I) are obtained when amides of the formula (II)

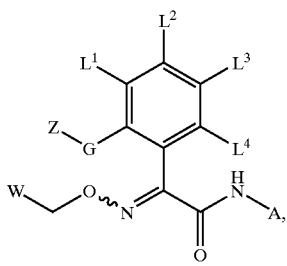

(II)

in which

A, G, $L^1$, $L^2$, $L^3$, $L^4$, W and Z are each as defined above, are reacted with an electrophilic reagent of the formula (III)

R—X (III)

in which

R is as defined above and

X represents a leaving group, if appropriate in the presence of a diluent and if appropriate in the presence of a base.

Finally, it has been found that the novel methoximinophenylacetamides of the general formula (I) have very strong fungicidal activity.

If appropriate, the compounds according to the invention can be present as mixtures of different possible isomeric forms, in particular of stereoisomers, such as, for example, E and Z or optical isomers. What is claimed are both the E and the Z isomers, the individual enantiomers, the racemates, and any mixtures of these isomers.

The present invention preferably provides methoximinophenylacetamides of the formula (I)

in which

A represents hydrogen, methyl, ethoxycarbonyl, ethyl or cyclopropyl, or has the same meaning as R, R represents alkylthio, halogenoalkylthio, alkoxycarbonylthio, alkylthiocarbonyl, having in each case 1 to 4 carbon atoms in the alkyl chains, represents phenylthio which is optionally substituted by halogen, cyano, alkyl, alkoxy or alkoxycarbonyl having in each case 1 to 4 carbon atoms, halogenoalkyl or halogenoalkoxy having in each case 1 to 4 carbon atoms and 1 to 9 identical or different halogen atoms, —S—Y, —S—N($R^1R^2$), —CO—N($R^3R^4$), —CN, —$CH_2$—O—$R^5$, —PO(O$R^6$)$R^7$, —PS(O$R^6$)$R^7$ where $R^1$ represents alkyl having 1 to 4 carbon atoms, $R^2$ represents alkyl having 1 to 4 carbon atoms, alkoxycarbonyl having 1 to 4 carbon atoms in the alkyl moiety, or together with $R^1$ and the nitrogen atom to which they are attached represents an optionally methyl- or ethyl-substituted heterocyclic ring having 5 or 6 ring members, $R^3$ represents alkyl having 1 to 4 carbon atoms or phenyl which is optionally substituted by halogen, alkyl or alkoxy having in each case 1 to 6 carbon atoms, halogenoalkyl or halogenoalkoxy having in each case 1 to 6 carbon atoms and 1 to 13 identical or different halogen atoms, $R^4$ represents alkylthio or alkylsulphonyl having in each case 1 to 4 carbon atoms or halogenoalkylthio having 1 to 4 carbon atoms and 1 to 5 identical or different halogen atoms or together with $R^3$ and the nitrogen atom to which they are attached represents an optionally methyl- or ethyl-substituted heterocyclic ring having 5 or 6 ring members, $R^5$ represents alkyl having 1 to 4 carbon atoms, $R^6$ represents alkyl having 1 to 4 carbon atoms, $R^7$ represents alkyl, alkoxy or alkylamino having in each case 1 to 4 carbon atoms in the alkyl chains, Y represents the same grouping which is already linked to the sulphur atom, or, if A represents methyl, R also represents alkylcarbonyl, alkoxycarbonyl, alkoxycarbonylcarbonyl, halogenoalkoxycarbonyl, alkylaminocarbonyl, dialkylaminocarbonyl, alkylsulphonyl having in each case 1 to 4 carbon atoms in the alkyl chains or phenylsulphonyl which is optionally substituted by alkyl having 1 to 4 carbon atoms, G represents a single bond, represents oxygen, sulphur or represents in each case optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or one of the groupings below in which in each case the left side is attached to Z:

—Q—CQ—, —CQ—Q—, —$CH_2$—Q—; —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^8$)=N—O—, —C($R^8$)=N—O—$CH_2$—, —N($R^9$)—, —CQ—N($R^9$)—, —N($R^9$)—CQ—, —Q—CQ—N($R^9$)—, —N=C($R^8$)—Q—$CH_2$—, —CH($R^8$)—O—N=CH—, —C($R^8$)=N—N=CH—, —N($R^9$)—CQ—Q—, —CQ—N($R^9$)—CQ—Q—, —N($R^9$)—CQ—Q—$CH_2$—, —Q—C($R^8$)=N—O—$CH_2$—, —N($R^9$)—C($R^8$)=N—O—$CH_2$—, —O—$CH_2$—C($R^8$)=N—O—$CH_2$—, —N=N—C($R^8$)=N—O—$CH_2$—, —C(=N—O—$R^{10}$)—C($R^8$)=N—O—$CH_2$—, —C(=N—O—$R^{10}$)—C($R^8$)—O—N=CH—, —C(=N—O—$R^{10}$)—C($R^8$)—N—N=CH—, —C(=N—O—$R^{10}$)—C($R^8$)—O—N=C(CH$_3$)—, —T—Ar$^1$— or —T—Ar$^1$—Q—, where n represents the number 0, 1 or 2, Q represents oxygen or sulphur, $R^8$ represents hydrogen, cyano, represents in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, $C_1$–$C_4$-alkyl- or $C_1$–$C_4$-alkoxycarbonyl-substituted cycloalkyl having 3 to 6 carbon atoms, and $R^9$ represents hydrogen, hydroxyl, cyano or represents optionally halogen-, cyano- or $C_1$–$C_4$-alkoxy-substituted alkyl having 1 to 6 carbon atoms or represents optionally halogen-, cyano-, carboxyl-, $C_1$–$C_4$-alkyl- or $C_1$–$C_4$-alkoxycarbonyl-substituted cycloalkyl having 3 to 6 carbon atoms, $R^{10}$ represents hydrogen, $C_1$–$C_4$-alkyl or benzyl which is optionally substituted by halogen, alkyl or alkoxy having in each case 1 to 6 carbon atoms, halogenoalkyl or halogenoalkoxy having in each case 1 to 6 carbon atoms and 1 to 13 identical or different halogen atoms, T represents a single bond, represents oxygen, sulphur, —$CH_2$—O—, —$CH_2$—S— or represents alkanediyl having 1 to 3 carbon atoms, $Ar^1$ represents phenylene, naphthylene, cycloalkylene, each of which is optionally mono- or polysubstituted by identical or different substituents or represents
  heteroarylene or heterocycloalkylene having 3 to 7 ring members, at least one of which represents oxygen, sulphur or nitrogen, and one or two more of which optionally represent nitrogen, where the possible substituents are preferably selected from the list below:
    halogen, cyano, nitro, amino, hydroxyl, formyl, carboxyl, carbamoyl, thiocarbamoyl;
    in each case straight-chain or branched alkyl, alkoxy, alkylthio, alkylsulphinyl or alkylsulphonyl having in each case 1 to 6 carbon atoms;
    in each case straight-chain or branched alkenyl or alkenyloxy having in each case 2 to 6 carbon atoms;
    in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
    in each case straight-chain or branched halogenoalkenyl or halogenoalkenyloxy having in each case 2 to 6 carbon atoms and 1 to 11 identical or different halogen atoms;
    in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and
    cycloalkyl having 3 to 6 carbon atoms,
$L^1$, $L^2$, $L^3$ and $L^4$ are identical or different and independently of one another each represent hydrogen, fluorine, chlorine, bromine, methyl, ethyl or n- of i-propyl, n-, i-, s-, or t-butyl,
W represents hydrogen, fluorine, cyano or thiocyanato and
Z represents alkyl having 1 to 8 carbon atoms which is optionally mono- or polysubstituted by identical or different substituents from the list consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (which may in each case optionally be substituted by halogen);
  represents in each case optionally halogen-substituted alkenyl or alkinyl having in each case up to 8 carbon atoms;
  tetrahydropyranyl;
  represents cycloalkyl having 3 to 6 carbon atoms which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;
  represents phenyl, naphthyl, tetrahydrobenzofuranyl, each of which is optionally mono- or polysubstituted by identical or different substituents, or represents heterocyclyl having 3 to 7 ring members, at least one of which represents oxygen, sulphur or nitrogen and one or two more of which optionally represent nitrogen, where the possible substituents are preferably selected from the list below:
    halogen, cyano, nitro, amino, hydroxyl, formyl, carboxyl, carbamoyl, thiocarbamoyl;
    in each case straight-chain or branched alkyl, alkoxy, alkylthio, alkylsulphinyl or alkylsulphonyl having in each case 1 to 6 carbon atoms;
    t-butyl-substituted tetrazole;
    in each case straight-chain or branched alkenyl or alkenyloxy having in each case 2 to 6 carbon atoms;
    in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms; phenyl;
    in each case straight-chain or branched halogenoalkenyl or halogenoalkenyloxy having in each case 2 to 6 carbon atoms and 1 to 11 identical or different halogen atoms;
    in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;
    in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;
    cycloalkyl having 3 to 6 carbon atoms;
    heterocyclyl or heterocyclyl-methyl having in each case 3 to 7 ring members, 1 to 3 of which are in each case identical or different heteroatoms—in particular nitrogen, oxygen and/or sulphur

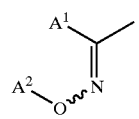

$A^1$ represents alkyl having 1 to 4 carbon atoms or cycloalkyl having 1 to 6 carbon atoms and
$A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

The present application relates in particular to methoximinophenylacetamides of the formula (I) in which
A represents hydrogen, methyl, ethoxycarbonyl, ethyl or cyclopropyl, or has the same meaning as R,
R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, 1,1-difluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N($R^1R^2$), —CO—N($R^3R^4$), —CN, —$CH_2$—O—$R^5$, —PO(O$R^6$)$R^7$, —PS(O$R^6$)$R^7$, in which $R^1$ represents methyl, ethyl, n- or i-propyl, n-, i-, s- or t-butyl, $R^2$ represents methyl, ethyl, n- or i-propyl, n-, i-, s- or t-butyl, methoxycarbonyl or ethoxycarbonyl, or together with $R^1$ and the nitrogen atom to which they are attached represents optionally methyl-or ethyl-substituted pyrrolidine, piperidine or morpholine, $R^3$ represents methyl, ethyl, n- or i-propyl, n-, i-, s- or t-butyl or represents phenyl which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, $R^4$ represents methylthio, ethylthio, n- or i-propylthio, n-, i-, s- or t- butylthio, methylsulphonyl, ethylsulphonyl, n- or i-propylsulphonyl, difluoromethylthio, trifluoromethylthio, difluorochloromethylthio, dichlorofluoromethylthio, trichloromethylthio or 2,2,2-trifluoroethylthio, or together with $R^3$ and the nitrogen atom to which they are attached represents optionally methyl- or ethyl-substituted pyrrolidine, piperidine or morpholine, $R^5$ represents methyl, ethyl, n- or i-propyl, n-, i-, s- or t-butyl, $R^6$ represents methyl, ethyl, n- or i-propyl, n-, i-, s- or t-butyl, $R^7$ represents methyl, ethyl, n- or i-propyl, n-, i-, s- or t-butyl, methoxy, etioxy, n- or i-propoxy, methylamino, ethylamino, dimethylamino or diethylamino, Y represents the same grouping which is already attached to the sulphur atom, or, if A represents methyl, R also represents acetyl, propionyl, methoxycarbonyl, ethoxycarbonyl, i-butoxycarbonyl, methoxycarbonylcarbonyl, 2-bromoethoxycarbonyl, methylaminocarbonyl, dimethylaminocarbonyl, methylsulphonyl, ethylsulphonyl, phenylsulphonyl or tolylsulphonyl, G represents oxygen or represents in each case optionally fluorine-, chlorine- or bromine-substituted dimethylene (ethane-1,2-diyl), ethene-1,2-diyl or one of the groupings below, in which in each case the left side is attached to Z:

—Q—CQ—, —CQ—Q—, —$CH_2$—Q—;
—Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^8$)=N—O—, —C($R^8$)=N—O—$CH_2$—, —N($R^9$)—, —CQ—N($R^9$)—, —N($R^9$)—CQ—, —Q—CQ—N($R^9$)—, —N=C($R^8$)—Q—$CH_2$—, —CH($R^8$)—O— N=CH—, —C($R^8$)=N—N=CH—, —N($R^9$)— CQ—Q—, —CQ—N($R^9$)—CQ—Q—, —N($R^9$)— CQ—Q—$CH_2$—, —Q—C($R^8$)=N—O—$CH_2$—, —N($R^9$)—C($R^8$)=N—O—$CH_2$—, —O—$CH_2$—C ($R^8$)=N—O—$CH_2$—, —N=N—C($R^8$)=N—O— $CH_2$—, —C(=N—O—$R^{10}$)—C($R^8$)=N—O— $CH_2$—, —C(=N—O—$R^{10}$)—C($R^8$)—O— N=CH—, —C(=N—O—$R^{10}$)—C($R^8$)—N— N=CH—, —C(=N—O—$R^{10}$)—C($R^8$)—O— N=C(CH$_3$)—, —T—Ar$^1$— or —T—Ar$^1$—Q—, where n represents the number 0, 1 or 2, Q represents oxygen or sulphur, $R^8$ represents hydrogen, cyano, methyl, ethyl or cyclopropyl and $R^9$ represents hydrogen, methyl, ethyl or cyclopropyl, $R^{10}$ represents hydrogen, methyl, ethyl, n- or i-propyl, n-, i-, s- or t-butyl or represents optionally fluorine-, chlorine-, bromine-, cyano-, methyl-, ethyl-, n- or i-propyl, n-, i-, s- or t-butyl-, methoxy-, ethoxy-, n- or i-propoxy-, trifluoromethyl-, trifluoroethyl-, difluoromethoxy-, trifluoromethoxy-, difluorochloromethoxy- or trifluoroethoxy-substituted benzyl, T represents a single bond, represents oxygen, sulphur, —$CH_2$—O—, —$CH_2$—S— or represents optionally substituted alkanediyl, Ar$^1$ represents phenylene or pyridinediyl, each of which is optionally mono- to trisubstituted by identical or different substituents, represents in each case optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, where the possible substituents are preferably selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and $L^1$, $L^2$, $L^3$ and $L^4$ are identical or different and independently of one another each represent hydrogen, fluorine, chlorine, bromine, methyl or ethyl, W represents hydrogen, fluorine, cyano or thiocyanato and Z represents methyl, ethyl, n- or i-propyl, n-, i-, s- or t-butyl, allyl, 2-buten-1-yl, 2-(1-methyl)-propyl, 2-methyl-2-buten-1-yl, propargyl, tetrahydropyranyl, t-butyl substituted tetrazole or represents phenyl, 1,2,4-thiadiazolyl, 1,3,4-thiadiazolyl, 1,2,4-oxadiazolyl, 1,3,4-oxadiazolyl, pyridinyl, pyrimidyl, tetrahydrobenzofuranyl, pyridazinyl, pyrazinyl, 1,2,3-triazinyl, 1,2,4-triazinyl or 1,3,5-triazinyl, each of which is optionally mono- to trisubstituted by identical or different substituents, where the possible substituents are preferably selected from the list below:

amino, fluorine, chlorine, bromine, iodine, cyano, nitro, methyl, ethyl, formyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, phenyl, in each case doubly attached methylenedioxy, ethylenedioxy, each of which is optionally mono- to tetrasubstituted by identical or different substituents from the group consisting of fluorine, chlorine, methyl, trifluoromethyl and ethyl,

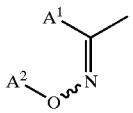

in which $A^1$ represents methyl, ethyl, n- or i-propyl, n-, i-, s- or t-butyl, cyclopropyl or cyclobutyl and $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

Independently of the abovementioned definitions, G also particularly preferably represents oxygen or one of the groupings below, in which in each case the left side is attached to Z: —Q—CH$_2$—, —C(R$^8$)=N—O—CH$_2$—, —N=C(R$^8$)—Q—CH$_2$—, —CH(R$^8$)—O—N=CH—, —C(R$^8$)=N—N=CH—, —C(=N—O—R$^{10}$)—C(R$^8$)=N—O—CH$_2$—, —C(=N—O—R$^{10}$)—C(R$^8$)—O—N=CH—, —C(=N—O—R$^{10}$)—C(R$^8$)—N—N=CH— or —T—Ar$^1$—Q—, where R$^8$, R$^9$, R$^{10}$, T, Ar$^1$ and Q each have the abovementioned preferred and particularly preferred meanings.

L$^1$, L$^2$, L$^3$ and L$^4$ independently of one another each particularly preferably represent hydrogen.

Q particularly preferably represents oxygen.

W particularly preferably represents hydrogen.

A particularly preferred group of compounds according to the invention are those compounds of the formula (I) in which A represents hydrogen, ethoxycarbonyl, methyl or ethyl, cyclopropyl, or has the same meaning as R, R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, 1,1-difluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N(R$^1$R$^2$), —CO—N(R$^3$R$^4$), —CN, —CH$_2$—O—R$^5$, —PO(OR$^6$)R$^7$, —PS(OR$^6$)R$^7$, in which R$^1$ represents methyl, ethyl, n- or i-propyl, n-, i-, s- or t-butyl, R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine, R$^3$ represents methyl, ethyl, n- or i-propyl, n-, i-, s- or t-butyl or represents phenyl which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, R$^4$ represents methylthio, ethylthio, n- or i-propylthio, n-, i-, s- or t-butylthio, methylsulphonyl, ethylsulphonyl, n- or i-propylsulphonyl, difluoromethylthio, trifluoromethylthio, difluorochloromethylthio, dichlorofluoromethylthio, trichloromethylthio or 2,2,2-trifluoroethylthio, or together with R$^3$ and the nitrogen atom to which they are attached represents optionally methyl- or ethyl-substituted pyrrolidine, piperidine or morpholine, R$^5$ represents methyl, ethyl, n- or i-propyl, n-, i-, s- or t-butyl, R$^6$ represents methyl, ethyl, n- or i-propyl, n-, i-, s- or t-butyl, R$^7$ represents methyl, ethyl, n- or i-propyl, n-, i-, s- or t-butyl, methoxy, ethoxy, n- or i-propoxy, methylamino, ethylamino, dimethylamino or diethylamino, Y represents the same grouping which is already attached to the sulphur atom, or, if A represents methyl, R also represents acetyl, propionyl, methoxycarbonyl, ethoxycarbonyl, i-butoxycarbonyl, methoxycarbonylcarbonyl, 2-bromoethoxycarbonyl, methylaminocarbonyl, dimethylaminocarbonyl, methylsulphonyl, ethylsulphonyl, phenylsulphonyl or tolylsulphonyl, G represents oxygen or, in particular, —O—CH$_2$—, L$^1$, L$^2$, L$^3$ and L$^4$ each represent hydrogen, W represents hydrogen, fluorine, cyano or thiocyanato and Z represents methyl, ethyl, n- or i-propyl, n-, i-, s- or t-butyl, allyl, 2-buten-1-yl, 2-methyl-2-buten-1-yl, propargyl, tetrahydropyranyl or represents phenyl which is in each case optionally mono- to trisubstituted by identical or different substituents, where the possible substituents are preferably selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, phenyl, in each case doubly attached methylenedioxy or ethylenedioxy, each of which is optionally mono- to tetrasubstituted by identical or different substituents from the group consisting of fluorine, chlorine, methyl, trifluoromethyl and ethyl,
or a grouping

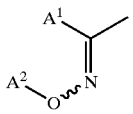

in which
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A group of compounds according to the invention that is likewise particularly preferred are those compounds of the formula (I)
in which
A represents hydrogen, ethyl or methyl, or has the same meaning as R,
R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N(R$^1$R$^2$), —CO—N(R$^3$R$^4$), —CN, —CH$_2$—O—R$^5$, —PO(OR$^6$)R$^7$, —PS(OR$^6$)R$^7$, in which
R$^1$ represents methyl, ethyl, n- or i-propyl, n-, i-, s- or t-butyl,
R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine,
R$^3$ represents methyl, ethyl, n- or i-propyl, n-, i-, s- or t-butyl or represents phenyl which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl,
R$^4$ represents methylthio, ethylthio, n- or i-propylthio, n-, i-, S- or t-butylthio, methylsulphonyl, ethylsulphonyl, n- or i-propylsulphonyl, difluoromethylthio, trifluoromethylthio, difluorochloromethylthio, dichlorofluoromethylthio, trichloromethylthio or 2,2,2-trifluoroethylthio, or together with R$^3$ and the nitrogen atom to which they are attached represents optionally methyl- or ethyl-substituted pyrrolidine, piperidine or morpholine,
R$^5$ represents methyl, ethyl, n- or i-propyl, n-, i-, s- or t-butyl,
R$^6$ represents methyl, ethyl, n- or i-propyl, n-, i-, s- or t-butyl,
R$^7$ represents methyl, ethyl, n- or i-propyl, n-, i-, s- or t-butyl, methoxy, ethoxy, n- or i-propoxy, methylamino, ethylamino, dimethylamino or diethylamino,
Y represents the same grouping which is already attached to the sulphur atom,
or, if A represents methyl,
R also represents acetyl, propionyl, methoxycarbonyl, ethoxycarbonyl, methoxycarbonylcarbonyl, 2-bromoethoxycarbonyl, methylaminocarbonyl, dimethylaminocarbonyl, methylsulphonyl, ethylsulphonyl, phenylsulphonyl or tolylsulphonyl,
G represents —C(R$^8$)=N—O—CH$_2$—,
R$^8$ represents cyclopropyl or, in particular, methyl,
L$^1$, L$^2$, L$^3$ and L$^4$ each represent hydrogen,
W represents hydrogen, fluorine, cyano or thiocyanato and
Z represents methyl, ethyl, n- or i-propyl, n-, i-, s- or t-butyl, allyl, 2-buten-1-yl, 2-methyl-2-buten-1-yl, propargyl or represents pyridyl, pyrimidyl or, in particular, phenyl, each of which is optionally mono- to trisubstituted by identical or different substituents where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy or ethylenedioxy, each of which is optionally mono- to tetrasubstituted by identical or different substituents from the group consisting of fluorine, chlorine, methyl, trifluoromethyl and ethyl.

A group of compounds according to the invention that is furthermore particularly preferred are those compounds of the formula (I)
in which
A represents hydrogen, ethyl or methyl, or has the same meaning as R,
R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N ($R^1R^2$), —CO—N($R^3R^4$), —CN, —CH$_2$—O—R$^5$, —PO(OR$^6$)R$^7$, —PS(OR$^6$)R$^7$, in which

- R$^1$ represents methyl, ethyl, n- or i-propyl, n-, i-, s- or t-butyl,
- R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine,
- R$^3$ represents methyl, ethyl, n- or i-propyl, n-, i-, s- or t-butyl or represents phenyl which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl,
- R$^4$ represents methylthio, ethylthio, n- or i-propylthio, n-, i-, s- or t-butylthio, methylsulphonyl, ethylsulphonyl, n- or i-propylsulphonyl, difluoromethylthio, trifluoromethylthio, difluorochloromethylthio, dichlorofluoromethylthio, trichloromethylthio or 2,2,2-trifluoroethylthio, or together with R$^3$ and the nitrogen atom to which they are attached represents optionally methyl- or ethyl-substituted pyrrolidine, piperidine or morpholine,
- R$^5$ represents methyl, ethyl, n- or i-propyl, n-, i-, s- or t-butyl,
- R$^6$ represents methyl, ethyl, n- or i-propyl, n-, i-, s- or t-butyl,
- R$^7$ represents methyl, ethyl, n- or i-propyl, n-, i-, s- or t-butyl, methoxy, ethoxy, n- or i-propoxy, methylamino, ethylamino, dimethylamino or diethylamino,
- Y represents the same grouping which is already attached to the sulphur atom, or, if A represents methyl,

- R also represents acetyl, propionyl, methoxycarbonyl, ethoxycarbonyl, methoxycarbonylcarbonyl, 2-bromoethoxycarbonyl, methylaminocarbonyl, dimethylaminocarbonyl, methylsulphonyl, ethylsulphonyl, phenylsulphonyl or tolylsulphonyl,
- G represents —T—Ar$^1$—O—,
  - Ar$^1$ represents 1,2,4-thiadiazoldiyl, 1,3,4-thiadiazoldiyl, 1,2,4-oxadiazoldiyl, 1,3,4-oxadiazoldiyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy, difluorochloromethoxy,
  - T represents a single bond, represents oxygen, sulphur, —CH$_2$—O—, CH$_2$—S—, methylene, ethylene or propylene and
- L$^1$, L$^2$, L$^3$ and L$^4$ each represent hydrogen,
- W represents hydrogen, fluorine, cyano or thiocyanato and
- Z represents methyl, ethyl, n- or i-propyl, n-, i-, s- or t-butyl, allyl, 2-buten-1-yl, 2-(1-methyl)-propyl, 2-methyl-2-buten-1-yl, propargyl or represents pyridyl, pyrimidyl, thienyl, tetrahydrobenzofuranyl or, in particular, phenyl, each of which is optionally mono- to trisubstituted by identical or different substituents from the group consisting of amino, fluorine, chlorine, bromine, iodine, cyano, nitro, methyl, formyl, ethyl, n- or i-propyl, n-, i-, s- or t-butyl, trifluoromethyl, t-butyl-substituted tetrazole, methoxy, ethoxy, n- or i-propoxy, difluoromethoxy, difluorochloromethoxy, trifluoroethoxy, trifluoromethoxy, methoximinoethyl, ethoximinomethyl, methoximinoethyl, ethoximinoethyl and in each case doubly attached methylenedioxy or ethylenedioxy, each of which is optionally mono- to tetrasubstituted by identical or different substituents from the group consisting of fluorine, chlorine, methyl, trifluoromethyl and ethyl.

Another particularly preferred group of compounds according to the invention are those compounds of the formula (I)
in which

- A represents hydrogen or methyl, or has the same meaning as R,
- R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N($R^1R^2$), —CO—N($R^3R^4$), —CN, —CH$_2$—O—R$^5$, —PO(OR$^6$)R$^7$, —PS(OR$^6$)R$^7$, in which
  - R$^1$ represents methyl, ethyl, n- or i-propyl, n-, i-, s- or t-butyl,
  - R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine,
  - R$^3$ represents methyl, ethyl, n- or i-propyl, n-, i-, s- or t-butyl or represents phenyl which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl,
  - R$^4$ represents methylthio, ethylthio, n- or i-propylthio, n-, i-, s- or t-butylthio, methylsulphonyl, ethylsulphonyl, n- or i-propylsulphonyl, difluoromethylthio, trifluoromethylthio, difluorochloromethylthio, dichlorofluoromethylthio, trichloromethylthio or 2,2,2-trifluoroethylthio, or together with R$^3$ and the nitrogen atom to which they are attached represents optionally methyl- or ethyl-substituted pyrrolidine, piperidine or morpholine,
  - R$^5$ represents methyl, ethyl, n- or i-propyl, n-, i-, s- or t-butyl,
  - R$^6$ represents methyl, ethyl, n- or i-propyl, n-, i-, s- or t-butyl,
  - R$^7$ represents methyl, ethyl, n- or i-propyl, n-, i-, s- or t-butyl, methoxy, ethoxy, n- or i-propoxy, methylamino, ethylamino, dimethylamino or diethylamino, Y represents the same grouping which is already attached to the sulphur atom, or, if A represents methyl, R also represents acetyl, propionyl, methoxycarbonyl, ethoxycarbonyl, methoxycarbonylcarbonyl, 2-bromoethoxycarbonyl, methylaminocarbonyl, dimethylaminocarbonyl, methylsulphonyl, ethylsulphonyl, phenylsulphonyl or tolylsulphonyl, G represents —C(=N—O—R$^{10}$)—C(R$^8$)=N—O—CH$_2$— in which R$^8$ represents methyl or cyclopropyl and R$^{10}$ represents hydrogen, methyl, ethyl, n- or i-propyl, n-, i-, s- or t-butyl or represents optionally fluorine-, chlorine-, bromine-, cyano-, methyl-, ethyl-, n- or i-propyl-, n-, i-, s- or t-butyl-, methoxy-, ethoxy-, n- or i-propoxy-, trifluoromethyl-, trifluoroethyl-, difluoromethoxy-, trifluoromethoxy-, difluorochloromethoxy- or trifluoroethoxy- substituted benzyl, L$^1$, L$^2$, L$^3$ and L$^4$ each represent hydrogen, W represents hydrogen, fluorine, cyano or thiocyanato and Z represents methyl, ethyl, n- or i-propyl, n-, i-, s- or t-butyl, allyl, 2-buten-1-yl, 2-methyl-2-buten-1-yl or represents pyridyl, pyrimidyl or, in particular, phenyl, each of which is optionally mono- to trisubstituted by identical or different substituents, where the possible substituents are preferably selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy, ethylenedioxy, each of which is optionally mono- to tetrasubstituted by identical or different substituents from the group consisting of fluorine, chlorine, methyl, trifluoromethyl and ethyl, or t-butyl-substituted tetrazole.

Particular preference is given to compounds of the formula (I)

in which

A represents methyl.

Particular preference is given to compounds of the formula (I)

in which

G represents oxygen, —O—CH$_2$, —C(CH$_3$)=N—O—CH$_2$— or optionally fluorine-substituted pyrimidinyloxy.

Particular preference is given to compounds of the formula (I)

in which

Z represents unsubstituted or mono- or disubstituted phenyl.

Particular preference is given to compounds of the formula (I)

in which

R represents the abovementioned substituents which are attached via sulphur, such as, in particular, alkyl-, halogenoalkyl-, optionally substituted phenyl-, alkoxycarbonyl- or dialkylaminothio.

Particular preference is given to compounds of the formula (I)

in which

W represents hydrogen.

Particular preference is given to compounds of the formula (I)

in which

L$^1$, L$^2$, L$^3$ and L$^4$ each represent hydrogen.

The abovementioned general or preferred radical definitions apply both to the end products of the formula (I) and also, correspondingly, to the starting materials or intermediates required in each case for the preparation.

These radical definitions can be combined with each other as desired, i.e. including combinations between the given ranges of preferred compounds.

The formula (II) provides a general definition of the amides required as starting materials for carrying out the process according to the invention for preparing the methoximinophenylacetamides of the formula (I). In this formula (II), A, G, L$^1$, L$^2$, L$^3$, L$^4$, W and Z each preferably or in particular have those meanings which have already been mentioned above, in connection with the description of the compounds of the formula (I) according to the invention, as being preferred or as being particularly preferred for A, G, L$^1$, L$^2$, L$^3$, L$^4$, W and Z.

The amides of the formula (I) are known and can be prepared by known methods (compare, for example, EP-A-398 692, EP-A-528 681, WO 98/21 189).

The formula (III) provides a definition of the electrophilic reagents furthermore required as starting materials for carrying out the process according to the invention for preparing the methoximinophenylacetamides of the formula (I). X represents a leaving group, such as, for example, halogen, preferably chlorine. If R represents alkylcarbonyl, carboxylic anhydrides are likewise suitable compounds of the formula (III), i.e. R represents -CO-R', where R' represents alkyl, preferably methyl or ethyl. If R represents alkylaminocarbonyl, the corresponding isocyanates are likewise suitable reagents of the formula (III).

All reagents of the formula (III) are known chemicals for synthesis, and the person skilled in the art knows which reagent is suitable for which particular case.

Suitable diluents for carrying out the process according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; or alcohols, such as tert-butanol.

The process according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, carbonates or bicarbonates, such as, for example, sodium hydride, potassium hydride, sodium amide, potassium tert-butoxide, sodium hydroxide, potassium hydroxide, sodium carbonate, potassium carbonate, potassium bicarbonate or sodium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures from −100° C. to 80° C., preferably at temperatures from −80° C. to 50° C.

When carrying out the process according to the invention for preparing the compounds of the formula (I), generally 1 to 3 mol, preferably 1 to 2 mol of electrophilic reagent of the formula (III) are employed per mole of the amide of the formula (II).

The practice of the reaction, and the work-up and isolation of the reaction products is carried out by generally known processes (compare also with the Preparation Examples).

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or

*Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Altemaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, Puccinia or Fusarium species, diseases in viticulture, fruit and vegetable growing, such as, for example, against Venturia, Sphaerotheca, Podosphaera and Plasmopara species, or rice diseases, such as for example, against Pyricularia species.

Furthermore, the compounds according to the invention may also be employed to increase the yield of crops. Moreover, they have reduced toxicity and are tolerated well by plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ for example organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their particular physical and/or chemical properties, the active compounds can be converted to the customary fonnulations, such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzarnide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl) ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-tiazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine mono-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, teclofialam, copper sulphate and other copper preparations.

Insecticides/Acaricide/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, bio-permethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoat, dimethylvinphos, diofenolan, disulfoton, Docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, Fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, Lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M,

*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyri-proxyfen, quinalphos, ribavirin, salithion, sebufos, silafluofen, spinosad, sulfotep, sulprofos, Tau-fluvalinate, tebufenozide, tebufenpyrad, tebupirimiphos, teflubenzuron, tefluthrin, temephos, temivinphos, terbufos, tetrachlorvinphos, Theta-cypermethrin, thiamethoxam, thiapronil, thiatriphos, Thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI 5302, Zeta-cypermethrin, zolaprofos, (1R-cis)-[5-(phenylmethyl)-3-fiuranyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, fertilizers and growth-regulating substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low-volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the active compound application rates are, in general, between 0.1 and 10,000 g/ha by weight, preferably between 10 and 1000 g/ha by weight. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

PREPARATION EXAMPLE

Example 1

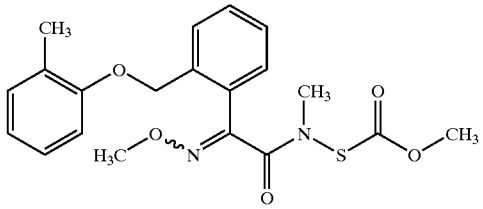

At from 0 to 5° C., 1.1 g (3.5 mmol) of 2-methoximino-2-[2-(methylphenoxy)-methylphenyl]-N-methyl-acetamide are added to a suspension of 0.17 g (4.2 mmol) of sodium hydride (60% in mineral oil) in 15 ml of tetrahydrofuran, and the mixture is stirred for 30 minutes. At −70° C. and with further cooling, 0.493 g (3.9 mmol) of methoxycarbonyl sulphinyl chloride is then added dropwise. The reaction mixture is subsequently stirred at room temperature overnight, inorganic material is filtered off and the solvent is distilled off under reduced pressure. The residue is chromatographed over silica gel using cyclohexane/ethyl acetate (3:1). This gives 1.24 g (88% of theory) of 2-methoximino-2-[2-(methylphenoxy)-methylphenyl]-N-methyl-N-methoxycarbonylthio-acetamide as a colourless oil.

HPLC: logP=4.25.

Example 2

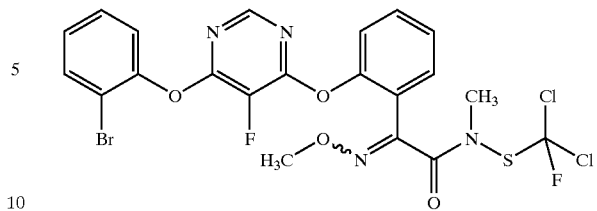

3.15 g (0.00663 mol) of 2-{2-[6-(2-bromophenoxy)-5-fluoropyrimidin-4-yloxy]-phenyl}-2-methoxyimino-N-methyl-acetamide are dissolved in 25 ml of pyridine and cooled to 0° C. 1.12 g (0.0066 mol) of dichlorofluoromethanesulphinyl chloride are added dropwise, and the mixture is subsequently stirred at 5° C. for 8 hours. The reaction mixture is poured into 200 ml of ice-cooled 2N hydrochloric acid and extracted with diethyl ether. The organic phase is dried over sodium sulphate and the solvent is distilled off under reduced pressure. The residue is chromatographed over silica gel using n-hexane: acetone=4:1. This gives 0.3 g (6.07% of theory; purity according to HPLC: 81.6%;) of 2-{2-[6-(2-bromo-phenoxy)-5-fluoro-pyrimidin-4-yloxy]-phenyl}-N-(dichlorofluoro-methyl-sulphanyl)-2-methoxyimino-N-methylacetamide.

logP=5.10;

LC/MS: M=614, 612, 611, 609, 607, 589, 577, 520, 489, 478, 477, 475, 459, 457, 388,366. $^1$H NMR spectrum (DMSOd$_6$/TMS): δ=3.35 (3H); 3.74 (3H); 7.29–7.34 (1H); 7.40–7.62 (6H); 7.78–7.81 (1H); 8.17 (1H) ppm.

By the methods of Examples 1 and 2, and in accordance with the general description of the preparation process according to the invention for preparing the compounds of formula (I), it was also possible to obtain the following compounds of the mula (Ia) according to the invention mentioned in Table 1:

TABLE 1

(Ia)

| Ex. | Z | G | R | A | W | logP | m.p. (° C.) |
|---|---|---|---|---|---|---|---|
| 3 | 2-chlorophenyl | 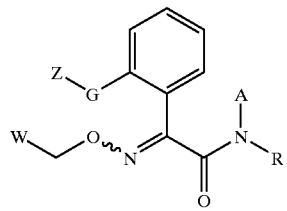 | —S—CCl$_2$F | —CH$_3$ | —H | 5.05 | |
| 4 | 2-tolyl | —O—CH$_2$— | —CN | —H | —H | 3.34 | 196 |
| 5 | 2-tolyl | —O—CH$_2$— | —S—CCl$_2$F | —CH$_3$ | —H | 5.35 | |
| 6 | 2-tolyl | —O—CH$_2$— | —S—CCl$_3$ | —CH$_3$ | —H | 5.56 | 65 |
| 7 | 2-tolyl | —O—CH$_2$— | 4-fluorophenylthio | —CH$_3$ | —H | 5.11 | |
| 8 | 2-tolyl | —O—CH$_2$— | —S—N(CH$_3$)—C(O)—O—CH$_3$ | —CH$_3$ | —H | 4.24 | |

TABLE 1-continued

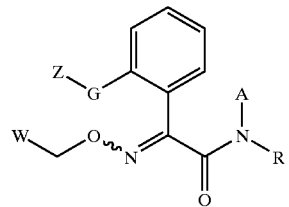

(Ia)

| Ex. | Z | G | R | A | W | logP | m.p. (° C.) |
|---|---|---|---|---|---|---|---|
| 9 | 2-tolyl | —O—CH$_2$— | —S—N(C$_4$H$_9$)$_2$ | —CH$_3$ | —H | 6.83 | |
| 10 | 2-tolyl | —O—CH$_2$— | —CN | —CH$_3$ | —H | 3.67 | |
| 11 | 2-tolyl | —O—CH$_2$— | 4-methoxyphenylthio | —CH$_3$ | —H | 4.98 | |
| 12 | 2-tolyl | —O—CH$_2$— | —COOC$_2$H$_5$ | —CH$_3$ | —H | 4.46 | |
| 13 | 2-tolyl | —O—CH$_2$— | 4-methoxycarbonyl-phenylthio | —CH$_3$ | —H | 4.89 | |
| 14 | 2-tolyl | —O—CH$_2$— | i-butyloxycarbonyl | —CH$_3$ | —H | 5.21 | |
| 15 | 2-tolyl | —O—CH$_2$— | P(=O)(O—C$_4$H$_9$)(OCH$_3$) | —CH$_3$ | —H | 4.53 | |
| 16 | 2-tolyl | —O—CH$_2$— | CH$_3$C(=O)N(CH$_3$)—S—CCl$_2$F | —CH$_3$ | —H | 5.08 | |
| 17 | 2-tolyl | —O—CH$_2$— | dimethylamino-carbonyl | —CH$_3$ | —H | 3.38 | |
| 18 | 2-tolyl | —O—CH$_2$— | —SO$_2$CH$_3$ | —CH$_3$ | —H | 3.82 | |
| 19 | 2-tolyl | —O—CH$_2$— | —CH$_2$—O—C$_2$H$_5$ | —CH$_3$ | —H | 4.02 | |
| 20 | 2-tolyl | —O—CH$_2$— | 4-chlorophenylthio | —CH$_3$ | —H | 5.53 | |
| 21 | 2-tolyl | —O—CH$_2$— | —S-phenyl | —CH$_3$ | —H | 5.11 | |
| 22 | 2-tolyl | —O—CH$_2$— | 3-trifluoromethyl-phenylthio | —CH$_3$ | —H | 5.5 | |
| 23 | 2-tolyl | —O—CH$_2$— | 3-chloro-4-trifluoro-methoxyphenylthio | —CH$_3$ | —H | 5.99 | |
| 24 | 2-tolyl | —O—CH$_2$— | 4-methylphenylthio | —CH$_3$ | —H | 5.45 | |
| 25 | 2-tolyl | —O—CH$_2$— | 4-chloro-3-trifluoro-methylphenylthio | —CH$_3$ | —H | 5.8 | |
| 26 | 2-tolyl | —O—CH$_2$— | —CO—CO—OCH$_3$ | —CH$_3$ | —H | 3.96 | |
| 27 | 2-tolyl | —O—CH$_2$— | —CO—S—C$_2$H$_5$ | —CH$_3$ | —H | 4.91 | |
| 28 | 2-tolyl | —O—CH$_2$— | —S—CCl$_2$F | —H | —H | 4.32 | |
| 29 | 2-tolyl | —O—CH$_2$— | —COOC$_2$H$_5$ | —COOC$_2$H$_5$ | —H | 4.42 | |
| 30 | 2-tolyl | —O—CH$_2$— | —COOC$_2$H$_5$ | —S—CCl$_2$F | —H | 5.35 | |
| 31 | 2-tolyl | —O—CH$_2$— | —CO—NH—CH$_3$ | —CH$_3$ | —H | 3.29 | |
| 32 | 3-trifluoro-methylphenyl | (CH$_3$)$_2$C=N—O—C$_2$H$_5$ | —S—CCl$_2$F | —CH$_3$ | —H | 5.74 | |
| 33 | 2-tolyl | —O—CH$_2$— | —COOCH$_3$ | —CH$_3$ | —H | 4.11 | |
| 34 | 2-tolyl | —O—CH$_2$— | CH$_3$C(=O)N(4-Cl-C$_6$H$_4$)—S—CCl$_2$F | —CH$_3$ | —H | 6.21 | |

TABLE 1-continued (Ia)

| Ex. | Z | G | R | A | W | logP | m.p. (° C.) |
|---|---|---|---|---|---|---|---|
| 35 | 2-tolyl | —O—CH$_2$— | N-acetyl-N-methyl-ethylsulfonamide group | —CH$_3$ | —H | 4.05 | |
| 36 | 2-tolyl | —O—CH$_2$— | 4-acetylmorpholine group | —CH$_3$ | —H | 3.32 | |
| 37 | 2-tolyl | —O—CH$_2$— | 2-bromoethyl acetate group | —CH$_3$ | —H | 4.6 | |
| 38 | 3-trifluoro-methylphenyl | (CH$_3$)C=N—O—ethyl | —COO—C$_2$H$_5$ | —CH$_3$ | —H | 4.91 | |
| 39 | 3-trifluoro-methylphenyl | (CH$_3$)C=N—O—ethyl | —CH$_2$—O—C$_2$H$_5$ | —CH$_3$ | —H | 4.58 | |
| 40 | 3-trifluoro-methylphenyl | (CH$_3$)C=N—O—ethyl | —S—COOCH$_3$ | —CH$_3$ | —H | 4.75 | |
| 41 | Phenyl | —O— | —COOC$_2$H$_5$ | —CH$_3$ | —H | 3.59 | |
| 42 | Phenyl | —O— | —CH$_2$—O—C$_2$H$_5$ | —CH$_3$ | —H | 3.36 | |
| 43 | Phenyl | —O— | —S—COOCH$_3$ | —CH$_3$ | —H | 3.59 | |
| 44 | 3-chloro-4-methyl-(trifluoromethoxy)phenyl | —O— | —S—CCl$_2$F | —CH$_3$ | —H | 5.87 | |
| 45 | bis-structure (dimer with S bridge) | | | | —H | 6.10 | |
| 46 | —CH$_2$—C$_2$F$_5$ | | 2,4-dimethoxypyrimidin-5-yl group; —S—CCl$_2$F | CH$_3$ | —H | 4.69 | |
| 47 | Phenyl | —O— | —S—CCl$_2$F | —CH$_3$ | —H | 4.75 | |

TABLE 1-continued (Ia)

| Ex. | Z | G | R | A | W | logP | m.p. (° C.) |
|---|---|---|---|---|---|---|---|
| 48 | Phenyl | —O— | 4-methoxy-phenylthio | —CH$_3$ | —H | 4.31 | |
| 49 | Phenyl | —O— | —CO—N(CH$_3$)—S—CCl$_2$F | —CH$_3$ | —H | 4.53 | |
| 50 | Phenyl | —O— | —S—CF$_3$ | —CH$_3$ | —H | 4.38 | |
| 51 | 2-tolyl | —O—CH$_2$— | —S—CCl$_2$F | —S—CCl$_2$F | —H | 6.61 | |
| 52 | 2-tolyl | —O—CH$_2$— | —S—C$_2$H$_5$ | —CH$_3$ | —H | 4.55 | |
| 53 | 2-tolyl | —O—CH$_2$— | —S—CCl$_2$F | —C$_2$H$_5$ | —H | 5.74 | |
| 54 | 2-tolyl | —O—CH$_2$— | —S—CH$_3$ | —CH$_3$ | —H | 4.22 | |
| 55 | 2-tolyl | —O—CH$_2$— | —S—(t-butyl) | —CH$_3$ | —H | 5.05 | |
| 56 | 2-tolyl | —O—CH$_2$— | —S—CF$_3$ | —CH$_3$ | —H | 4.93 | |
| 57 | 2-tolyl | —O—CH$_2$— | —S—CF$_2$—CH$_3$ | —CH$_3$ | —H | 4.62 | |
| 58 | 2-ethylthio-methylphenyl | —O—CH$_2$— | —S—CCl$_2$F | —CH$_3$ | —H | 5.59 | |
| 59 | 2-tolyl | —O—CH$_2$— | —CO—N(CH$_3$)S—CF$_3$ | —CH$_3$ | —H | 4.75 | |
| 60 | 2-tolyl | —O—CH$_2$— | —S—CCl$_2$F | cyclopropyl | —H | 5.58 | |
| 61 | 2-tolyl | —O—CH$_2$— | —S—CF$_3$ | cyclopropyl | —H | 5.17 | |
| 62 | 2-tolyl | —O—CH$_2$— | —S—CF$_3$ | —C$_2$H$_5$ | —H | 5.3 | |
| 63 | (3,4-dimethylphenyl C(CH$_3$)=N—O—CH$_3$) | —O—CH$_2$— | —S—CCl$_2$F | —CH$_3$ | —H | 5.69 | |
| 64 | (3,4-dimethylphenyl C(CH$_3$)=N—O—CH$_3$) | —O—CH$_2$— | —S—CF$_3$ | —CH$_3$ | —H | 5.27 | |
| 65 | 3-phenylphenyl | —O—CH$_2$— | —S—CCl$_2$F | —CH$_3$ | —H | 5.77 | |
| 66 | 3-phenylphenyl | —O—CH$_2$— | —S—CF$_3$ | —CH$_3$ | —H | 5.36 | |
| 67 | 2,5-dimethyl-phenyl | —O—CH$_2$— | —S—CCl$_2$F | —CH$_3$ | —H | 5.68 | |
| 68 | 2,5-dimethyl-phenyl | —O—CH$_2$— | —S—CF$_3$ | —CH$_3$ | —H | 5.25 | |
| 69 | 2,5-difluoro-phenyl | —O—CH$_2$— | —S—CCl$_2$F | —CH$_3$ | —H | 4.86 | |
| 70 | 2,5-difluoro-phenyl | —O—CH$_2$— | —S—CF$_3$ | —CH$_3$ | —H | 4.48 | |
| 71 | 3-trifluoro-methylphenyl | (CH$_3$)$_2$C=N—O—ethyl | —S—CH$_3$ | —CH$_3$ | —H | 4.73 | |
| 72 | 3-trifluoro-methylphenyl | (CH$_3$)$_2$C=N—O—ethyl | —S-phenyl | —CH$_3$ | —H | 5.48 | |

TABLE 1-continued (Ia)

| Ex. | Z | G | R | A | W | logP | m.p. (° C.) |
|---|---|---|---|---|---|---|---|
| 73 | 3-trifluoro-methylphenyl | CH₃-C(=N-O-ethyl)- | —S—C₂H₅ | —CH₃ | —H | 5.02 | |
| 74 | 3-trifluoro-methylphenyl | CH₃-C(=N-O-ethyl)- | 3-trifluoro-methylphenylthio | —CH₃ | —H | 5.84 | |
| 75 | 3-trifluoro-methylphenyl | CH₃-C(=N-O-ethyl)- | —S—CF₃ | —CH₃ | —H | 5.36 | |
| 76 | 3-trifluoro-methylphenyl | CH₃-C(=N-O-ethyl)- | —CO—N(CH₃)—S—CF₃ | —CH₃ | —H | 5.22 | |
| 77 | 3-chlorophenyl | CH₃-C(=N-O-ethyl)- | —S—CCl₂F | —CH₃ | —H | 5.79 | |
| 78 | 3-chlorophenyl | CH₃-C(=N-O-ethyl)- | —S—CF₃ | —CH₃ | —H | 5.39 | |
| 79 | 3,4-dimethoxyphenyl | CH₃-C(=N-O-ethyl)- | —S—CCl₂F | —CH₃ | —H | 4.7 | |
| 80 | 3,4-dimethoxyphenyl | CH₃-C(=N-O-ethyl)- | —S—CF₃ | —CH₃ | —H | 4.36 | |
| 81 | 3-chlorophenyl | CH₃-C(=N-O-ethyl)- | —S—COOCH₃ | —CH₃ | —H | 4.71 | |
| 82 | 3,4-dimethoxyphenyl | CH₃-C(=N-O-ethyl)- | —S—COOCH₃ | —CH₃ | —H | 3.7 | |
| 83 | 3-fluorophenyl | CH₃-C(=N-O-ethyl)- | —S—CCl₂F | —CH₃ | —H | 5.36 | |
| 84 | 3-fluorophenyl | CH₃-C(=N-O-ethyl)- | —S—CF₃ | —CH₃ | —H | 4.97 | |

TABLE 1-continued
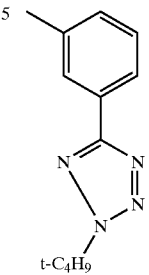
(Ia)
| Ex. | Z | G | R | A | W | logP | m.p. (° C.) |
|---|---|---|---|---|---|---|---|
| 85 | 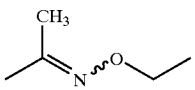 | 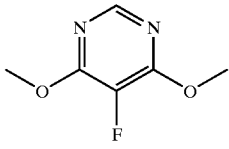 | —S—CCl$_2$F | —CH$_3$ | —H | | |
| 86 | 3-chloro-2-methylphenyl |  | —S—CCl$_2$F | —CH$_3$ | —H | 5.59 | 128–130 |
| 87 | 2-chloro-3-formylphenyl | 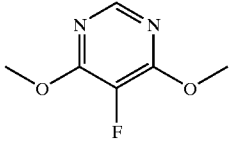 | —S—CCl$_2$F | —CH$_3$ | —H | 4.72 | |
| 88 | phenyl | 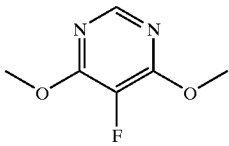 | —S—CCl$_2$F | —CH$_3$ | —H | 4.76 | |
| 89 | 2-tolyl | 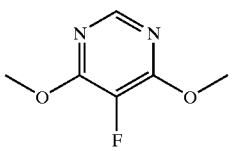 | —S—CCl$_2$F | —CH$_3$ | —H | 5.05 | |
| 90 | 2,4-dimethylphenyl | 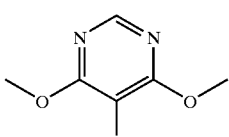 | —S—CCl$_2$F | —CH$_3$ | —H | 5.41 | |
| 91 | 2,3-dichlorophenyl |  | —S—CCl$_2$F | —CH$_3$ | —H | 5.46 | |

TABLE 1-continued (Ia)

| Ex. | Z | G | R | A | W | logP | m.p. (° C.) |
|---|---|---|---|---|---|---|---|
| 92 | 2,3-dimethylphenyl | 4,6-dimethoxy-5-fluoropyrimidin-2-yl | —S—CCl$_2$F | —CH$_3$ | —H | 5.34 | |
| 93 | 2-trifluoromethoxyphenyl | 4,6-dimethoxy-5-fluoropyrimidin-2-yl | —S—CCl$_2$F | —CH$_3$ | —H | 5.2 | |
| 94 | 2-difluoromethoxyphenyl | 4,6-dimethoxy-5-fluoropyrimidin-2-yl | —S—CCl$_2$F | —CH$_3$ | —H | 4.7 | |
| 95 | 2-ethylthiomethylphenyl | 4,6-dimethoxy-5-fluoropyrimidin-2-yl | —S—CCl$_2$F | —CH$_3$ | —H | 5.36 | |
| 96 | 2,2-dimethyl-7-methyl-2,3-dihydrobenzofuran-4-yl | 4,6-dimethoxy-5-fluoropyrimidin-2-yl | —S—CCl$_2$F | —CH$_3$ | —H | 5.27 | |
| 97 | 2,6-dimethylphenyl | 4,6-dimethoxy-5-fluoropyrimidin-2-yl | —S—CCl$_2$F | —CH$_3$ | —H | 5.4 | |
| 98 | 2-chlorophenyl | 4,6-dimethoxy-5-fluoropyrimidin-2-yl | —S—CCl$_2$F | —CH$_3$ | —F | 4.84 | |
| 99 | 2-chloro-4-trifluoromethoxyphenyl | 4,6-dimethoxy-5-fluoropyrimidin-2-yl | —S—CCl$_2$F | —CH$_3$ | —H | 5.08 | |

TABLE 1-continued (Ia)

| Ex. | Z | G | R | A | W | logP | m.p. (° C.) |
|---|---|---|---|---|---|---|---|
| 100 | 3-methoxyimino-methylphenyl | 4,6-dimethoxy-5-fluoropyrimidin-2-yl | —S—CCl₂F | —CH₃ | —H | 5.81 | |
| 101 | 3-bromophenyl | 4,6-dimethoxy-5-fluoropyrimidin-2-yl | —S—CCl₂F | —CH₃ | —H | 5.39 | |
| 102 | 2,4-dichlorophenyl | 4,6-dimethoxy-5-fluoropyrimidin-2-yl | —S—CCl₂F | —CH₃ | —H | 5.76 | |
| 103 | 3,5-dichlorophenyl | 4,6-dimethoxy-5-fluoropyrimidin-2-yl | —S—CCl₂F | —CH₃ | —H | 5.71 | |
| 104 | 4-bromophenyl | 4,6-dimethoxy-5-fluoropyrimidin-2-yl | —S—CCl₂F | —CH₃ | —H | 5.19 | |
| 105 | 2-fluorophenyl | 4,6-dimethoxy-5-fluoropyrimidin-2-yl | —S—CCl₂F | —CH₃ | —H | 4.73 | |
| 106 | 3-trifluoro-methylphenyl | 4,6-dimethoxy-5-fluoropyrimidin-2-yl | —S—CCl₂F | —CH₃ | —H | 5.11 | |
| 107 | 4-cyanophenyl | 4,6-dimethoxy-5-fluoropyrimidin-2-yl | —S—CCl₂F | —CH₃ | —H | 4.34 | |

TABLE 1-continued (Ia)

| Ex. | Z | G | R | A | W | logP | m.p. (° C.) |
|---|---|---|---|---|---|---|---|
| 108 | 4-methoxyphenyl | 4,6-dimethoxy-5-fluoropyrimidin-2-yl | —S—CCl$_2$F | —CH$_3$ | —H | 4.63 | |
| 109 | 2-ethylphenyl | 4,6-dimethoxy-5-fluoropyrimidin-2-yl | —S—CCl$_2$F | —CH$_3$ | —H | 5.25 | |
| 110 | 2-ethoxyphenyl | 4,6-dimethoxy-5-fluoropyrimidin-2-yl | —S—CCl$_2$F | —CH$_3$ | —H | 4.86 | |
| 111 | 2-(t-butyl)-phenyl | 4,6-dimethoxy-5-fluoropyrimidin-2-yl | —S—CCl$_2$F | —CH$_3$ | —H | 5.73 | |
| 112 | 2-methoxy-4-trifluoromethylphenyl | 4,6-dimethoxy-5-fluoropyrimidin-2-yl | —S—CCl$_2$F | —CH$_3$ | —H | 5.16 | |
| 113 | 3-methyl-2-nitrophenyl | 4,6-dimethoxy-5-fluoropyrimidin-2-yl | —S—CCl$_2$F | —CH$_3$ | —H | 4.71 | |
| 114 | 2-chloro-4-fluorophenyl | 4,6-dimethoxy-5-fluoropyrimidin-2-yl | —S—CCl$_2$F | —CH$_3$ | —H | 5.14 | |
| 115 | 3,4-dichlorophenyl | 4,6-dimethoxy-5-fluoropyrimidin-2-yl | —S—CCl$_2$F | —CH$_3$ | —H | 5.58 | |

TABLE 1-continued (Ia)

| Ex. | Z | G | R | A | W | logP | m.p. (° C.) |
|---|---|---|---|---|---|---|---|
| 116 | 2,4-difluorophenyl | 4,6-dimethoxy-5-fluoropyrimidin-2-yl | —S—CCl$_2$F | —CH$_3$ | —H | 4.85 | |
| 117 | 3-chlorophenyl | 4,6-dimethoxy-5-fluoropyrimidin-2-yl | —S—CCl$_2$F | —CH$_3$ | —H | 5.14 | |
| 118 | 3-fluorophenyl | 4,6-dimethoxy-5-fluoropyrimidin-2-yl | —S—CCl$_2$F | —CH$_3$ | —H | 4.76 | |
| 119 | 2-cyanophenyl | 4,6-dimethoxy-5-fluoropyrimidin-2-yl | —S—CCl$_2$F | —CH$_3$ | —H | 4.28 | |
| 120 | 4-tolyl | 4,6-dimethoxy-5-fluoropyrimidin-2-yl | —S—CCl$_2$F | —CH$_3$ | —H | 5.02 | |
| 121 | 2,5-dimethylphenyl | 4,6-dimethoxy-5-fluoropyrimidin-2-yl | —S—CCl$_2$F | —CH$_3$ | —H | 5.34 | |
| 122 | 2-allylphenyl | 4,6-dimethoxy-5-fluoropyrimidin-2-yl | —S—CCl$_2$F | —CH$_3$ | —H | 5.3 | |
| 123 | 2-(i-propyl)phenyl | 4,6-dimethoxy-5-fluoropyrimidin-2-yl | —S—CCl$_2$F | —CH$_3$ | —H | 5.56 | |

TABLE 1-continued (Ia)

| Ex. | Z | G | R | A | W | logP | m.p. (° C.) |
|---|---|---|---|---|---|---|---|
| 124 | 2-isopropyl-5-methylphenyl | 4,6-dimethoxy-5-fluoropyrimidin-2-yl | —S—CCl₂F | —CH₃ | —H | 5.88 | |
| 125 | 3-chloro-6-methylphenyl | 4,6-dimethoxy-5-fluoropyrimidin-2-yl | —S—CCl₂F | —CH₃ | —H | 5.46 | |
| 126 | 2-chloro-3-trifluoro-methylphenyl | 4,6-dimethoxy-5-fluoropyrimidin-2-yl | —S—CCl₂F | —CH₃ | —H | 5.42 | |
| 127 | 4-iodophenyl | 4,6-dimethoxy-5-fluoropyrimidin-2-yl | —S—CCl₂F | —CH₃ | —H | 5.35 | |
| 128 | 3-tolyl | 4,6-dimethoxy-5-fluoropyrimidin-2-yl | —S—CCl₂F | —CH₃ | —H | 4.98 | |
| 129 | 2-methoxyphenyl | 4,6-dimethoxy-5-fluoropyrimidin-2-yl | —S—CCl₂F | —CH₃ | —H | 4.57 | |
| 130 | 3-methoxyphenyl | 4,6-dimethoxy-5-fluoropyrimidin-2-yl | —S—CCl₂F | —CH₃ | —H | 4.68 | |
| 131 | 4-ethylphenyl | 4,6-dimethoxy-5-fluoropyrimidin-2-yl | —S—CCl₂F | —CH₃ | —H | 5.38 | |

TABLE 1-continued (Ia)

| Ex. | Z | G | R | A | W | logP | m.p. (° C.) |
|---|---|---|---|---|---|---|---|
| 132 | 3-(t-butyl)phenyl | 4,6-dimethoxy-5-fluoropyrimidin-2-yl | —S—CCl$_2$F | —CH$_3$ | —H | 5.84 | |
| 133 | 4-trifluoro-methoxyphenyl | 4,6-dimethoxy-5-fluoropyrimidin-2-yl | —S—CCl$_2$F | —CH$_3$ | —H | 5.3 | |
| 134 | 2-(1-methyl)-propylphenyl | 4,6-dimethoxy-5-fluoropyrimidin-2-yl | —S—CCl$_2$F | —CH$_3$ | —H | 5.86 | |
| 135 | 2-methyl-5-(2-t-butyltetrazolyl)phenyl | 4,6-dimethoxy-5-fluoropyrimidin-2-yl | —S—CCl$_2$F | —CH$_3$ | —H | 5.27 | |
| 136 | 4-amino-2,3-dichlorophenyl | 4,6-dimethoxy-5-fluoropyrimidin-2-yl | —S—CCl$_2$F | —CH$_3$ | —H | 4.68 | |
| 137 | 3-ethyl-5-methylphenyl | 4,6-dimethoxy-5-fluoropyrimidin-2-yl | —S—CCl$_2$F | —CH$_3$ | —H | 5.76 | |
| 138 | 2-methyl-4-trifluoro-methoxyphenyl | 4,6-dimethoxy-5-fluoropyrimidin-2-yl | —S—CCl$_2$F | —CH$_3$ | —H | 5.65 | |

TABLE 1-continued (Ia)

[Structure: phenyl ring with Z-G substituent at ortho position, attached to C(=NOCH₂-W)-C(=O)-N(A)(R)]

| Ex. | Z | G | R | A | W | logP | m.p. (° C.) |
|---|---|---|---|---|---|---|---|
| 139 | 4-trifluoro-methylthiophenyl | 4,6-dimethoxy-5-fluoropyrimidin-2-yl | —S—CCl₂F | —CH₃ | —H | 5.6 | |
| 140 | 2-methoxyimino-methylphenyl | 4,6-dimethoxy-5-fluoropyrimidin-2-yl | —S—CCl₂F | —CH₃ | —H | 5.03 | |
| 141 | 3-chloro-2-methylphenyl | 4,6-dimethoxypyrimidin-2-yl | —S—CCl₂F | —CH₃ | —H | 5.29 | 128.0 |
| 142 | 2-tetrahydropyranyl | —O— | —S—CCl₂F | —CH₃ | —F | | Oil |
| 143 | phenyl | [2-(methoxyimino)-3-(methoxyimino)butan-2,3-diyl group] | —S—CCl₂F | —CH₃ | —H | 5.48 | |
| 144 | 2,6-difluorophenyl | —CO—O— | —S—CCl₂F | —CH₃ | —H | 4.41 | 79 |
| 145 | —CH₃ | 4,6-dimethoxy-5-fluoropyrimidin-2-yl | —S—CCl₂F | —CH₃ | —H | 5.45 | |
| 146 | —CH₃ | —O— | —S—CCl₂F | —CH₃ | —H | 3.69 | |

*) The logP values were determined in accordance with EEC-Directive 79/831 Annex V. A8 by HPLC (gradient method, acetonitrile/0.1% aqueous phosphoric acid)

Use Examples

EXAMPLE A

Plasmopara Test (Grapevine)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention listed in Examples (1), (3), (5), (6), (7), (8), (9), (11), (13), (20), (21), (22), (23), (24), (25), (26), (32), (40), (44), (46), (52), (54), (55), (56), (57), (61), (63), (64), (66), (67), (68), (69), (70), (71), (72), (73), (75), (86), (88), (91), (92), (93), (97), (100), (101), (102), (105), (106), (109), (117), (128), (141) and (143) exhibit, at an application rate of 100 g/ha, an efficacy of 90% or more.

Example B
Podosphaera Test (Apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, the substances according to the invention listed in Examples (1), (5), (6), (7), (10), (11), (13), (20), (21), (22), (23), (26), (32), (40), (46), (52), (54), (56), (57), (61), (64), (66), (67), (68), (69), (70), (72), (75), (86), (88), (91), (92), (100), (101), (141) and (143) exhibit, at an application rate of 100 g/ha, an efficacy of 90% or more.

Example C
Sphaerotheca Test (Cucumber)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuiginea*. The plants are then placed in the greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, the substances according to the invention listed in Examples (1), (3), (5), (6), (7), (8), (9), (11), (12), (13), (20), (21), (22), (23), (24), (25), (26), (32), (40), (44), (45), (46), (52), (54), (55), (56), (57), (61), (63), (64), (66), (67), (68), (69), (71), (72), (73), (75), (86), (88), (91), (92), (93), (97), (100), (101), (102), (105), (106), (109), (117), (128), (141) and (143) exhibit, at an application rate of 100 g/ha, an efficacy of 90% or more.

Example D
Venturia Test (Apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, the substances according to the invention listed in Examples (1), (3), (5), (6), (7), (8), (9), (10), (11), (12), (13), (14), (15), (20), (21), (22), (23), (24), (25), (26), (32), (40), (44), (52), (54), (55), (56), (57), (63), (64), (66), (71), (72), (73), (75), (86), (88), (91), (92), (93), (97), (100), (101), (102), (105), (106), (109), (117), (128), (141) and (143) exhibit, at an application rate of 10 g/ha, an efficacy of 90% or more.

Example E
Fusarium Nivale (var. Nivale) Test (Wheat)/Protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the sprayed coating has dried on, the plants are sprayed with a conidia suspension of Fusarium nivale (var. nivale).

The plants are placed in a greenhouse under transparent incubation hoods at a temperature of approximately 15° C. and a relative atmospheric humidity of approximately 100%.

Evaluation is carried out 4 days after the inoculation. 0% means an efficacy which corresponds to that of the control, whereas an efficacy of 100% means that no infection is observed.

In this test, the substances according to the invention listed in Examples (5), (67), (68), (100), (101.), (102), (103), (104), (105), (106), (109), (114), (115), (116), (117), (118), (119), (120), (121), (122), (123), (124), (125), (126), (130), (134), (138), and (139) exhibit, at an application rate of 250 g/ha, an efficacy of 90% or more.

Example F
Erysiphe Test (Barley)/Curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. hordei. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew postules.

Evaluation is carried out 7 days after the inoculation. 0% means an efficacy which corresponds to that of the control, whereas an efficacy of 100% means that no infection is observed.

In this test, the substances according to the invention listed in Examples (5), (67), (68), (100), (101), (102), (103), (106), (107), (108), (109), (110), (113), (114), (115), (116), (117), (119), (123), (124) and (128) exhibit, at an application rate of 250 g/ha, an efficacy of 90% or more.

What is claimed is:

1. A compound of the formula (I),

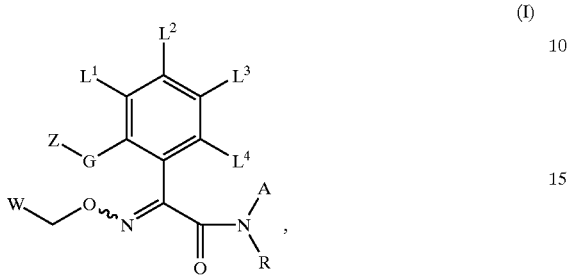

in which

A represents hydrogen, methyl, ethoxycarbonyl, ethyl or cyclopropyl, or has the same meaning as R, R represents alkylthio, halogenoalkylthio, alkoxycarbonylthio, having in each case 1 to 4 carbon atoms in the alkyl chains, represents phenylthio which is optionally substituted by halogen, cyano, alkyl, alkoxy or alkoxycarbonyl having in each case 1 to 4 carbon atoms, halogenoalkyl or halogenoalkoxy having in each case 1 to 4 carbon atoms and 1 to 9 identical or different halogen atoms, —S—Y, —S—N($R^1R^2$), where $R^1$ represents alkyl having 1 to 4 carbon atoms, $R^2$ represents alkyl having 1 to 4 carbon atoms, alkoxycarbonyl having 1 to 4 carbon atoms in the alkyl moiety, or together with $R^1$ and the nitrogen atom to which they are attached represents an optionally methyl- or ethyl-substituted heterocyclic ring having 5 or 6 ring members, Y represents the same grouping which is already linked to the sulphur atom, G represents a single bond, represents oxygen, sulphur or represents in each case optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or one of the groupings below in which in each case the left side is attached to Z:

—Q—CQ—, —CQ—Q—, —$CH_2$—Q—; —Q—$CH_2$—, —CQ—Q—$CH_2$—, —$CH_2$—Q— CQ—, —Q—CQ—$CH_2$—, —Q—CQ—Q— $CH_2$—, —N=N—, —S(O)$_n$—, —$CH_2$—S(O)$_n$—, —CQ—, —S(O)$_n$—$CH_2$—, —C($R^8$)=N—O—, —C($R^8$)=N—O—$CH_2$—, —N($R^9$)—, —CQ—N ($R^9$)—, —N($R^9$)—CQ—, —Q—CQ—N($R^9$)—, —N=C($R^8$)—Q—$CH_2$—, —CH($R^8$)—O— N=CH—, —C($R^8$)=N—N=CH—, —N($R^9$)— CQ—Q—, —CQ—N($R^9$)—CQ—Q—, —N($R^9$)— CQ—Q—$CH_2$—, —Q—C($R^8$)=N—O—$CH_2$—, —N($R^9$)—C($R^8$)=N—O—$CH_2$—, —O—$CH_2$—C ($R^8$)=N—O—$CH_2$—, —N=N—C($R^8$)=N—O— $CH_2$—, —C(=N—O—$R^{10}$)—C($R^8$)=N—O— $CH_2$—, —C(=N—O—$R^{10}$)—C($R^8$)=O— N=CH—, —C(=N—O—$R^{10}$)—C($R^8$)—N— N=CH—, —C(=N—O—$R^{10}$)—C($R^8$)=O— N=C($CH_3$)—, —T—$Ar^1$— or —T—$Ar^1$—Q—, where n represents the number 0, 1 or 2, Q represents oxygen or sulphur, $R^8$ represents hydrogen, cyano, represents in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, $C_1$–$C_4$-alkyl- or $C_1$–$C_4$-alkoxycarbonyl-substituted cycloalkyl having 3 to 6 carbon atoms, and $R^9$ represents hydrogen, hydroxyl, cyano or represents optionally halogen-, cyano- or $C_1$–$C_4$-alkoxy-substituted alkyl having 1 to 6 carbon atoms or represents optionally halogen-, cyano-, carboxyl-, $C_1$–$C_4$-alkyl- or $C_1$–$C_4$-alkoxycarbonyl-substituted cycloalkyl having 3 to 6 carbon atoms, $R^{10}$ represents hydrogen, $C_1$–$C_4$-alkyl or benzyl which is optionally substituted by halogen, alkyl or alkoxy having in each case 1 to 6 carbon atoms, halogenoalkyl or halogenoalkoxy having in each case 1 to 6 carbon atoms and 1 to 13 identical or different halogen atoms, T represents a single bond, represents oxygen, sulphur, —$CH_2$—O—, —$CH_2$—S— or represents alkanediyl having 1 to 3 carbon atoms, $Ar^1$ represents phenylene, naphthylene, cycloalkylene, each of which is optionally mono- or polysubstituted by identical or different substituents or represents heteroarylene or heterocycloalkylene having 3 to 7 ring members, at least one of which represents oxygen, sulphur or nitrogen, and one or two more of which optionally represent nitrogen, where the possible substituents are preferably selected from the list below: halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 1 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 1 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and cycloalkyl having 3 to 6 carbon atoms and $L^1$, $L^2$, $L^3$ and $L^4$ are identical or different and independently of one another each represent hydrogen, fluorine, chlorine, bromine, methyl, ethyl or n-, i-propyl, n-, i-, s-, or t-butyl, W represents hydrogen, fluorine, cyano or thiocyanato and Z represents alkyl having 1 to 8 carbon atoms which is optionally mono- or polysubstituted by identical or different substituents from the list consisting of halogen, cyano, hydroxyl, amino, $C_1$–$C_4$-alkoxy, C1–$C_4$-alkylthio, $C_1$–$C_4$-alkylsulphinyl and $C_1$–$C_4$-alkylsulphonyl (which may in each case optionally be substituted by halogen);

represents in each case optionally halogen-substituted alkenyl or alkynyl having in each case up to 8 carbon atoms;

tetrahydropyranyl;

represents cycloalkyl having 3 to 6 carbon atoms which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), C1–$C_4$-alkyl and C1–$C_4$-alkoxy-carbonyl;

represents phenyl, naphthyl, tetrahydrobenzofuranyl, each of which is optionally mono- or polysubstituted by identical or different substituents, or represents heterocyclyl having 3 to 7 ring members, at least one of which represents oxygen, sulphur or nitrogen and one or two more of which optionally represent nitrogen, where the possible substituents are preferably selected from the list below:

halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, alogenoalkylthio, halogenoalkylsulphinyl or halogenoalkylsulphonyl having in each case 1 to 6 carbon atoms and 1 to 13 identical or different halogen atoms;

t-butyl-substituted tetrazole;

in each case straight-chain or branched halogenoalkenyl or halogenoalkenyloxy having in each case 1 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;

phenyl;

in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different heteroatoms—in particular nitrogen, oxygen and/or sulphur—or a grouping

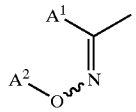

in which
A[1] represents alkyl having 1 to 4 carbon atoms or cycloalkyl having 1 to 6 carbon atoms and
A[2] represents optionally cyano-, alkoxy-, alkylthio-, alkylamino-, dialkylamino- or phenyl-substituted alkyl having 1 to 4 carbon atoms, alkenyl or alkynyl having in each case 2 to 4 carbon atoms.

2. A compound of the formula (I) according to claim 1 in which

A represents hydrogen, methyl, ethoxycarbonyl, ethyl or cyclopropyl, or has the same meaning as R, R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, 1,1-difluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N($R^1R^2$), in which
$R^1$ represents methyl, ethyl, n- or i-propyl, n-, i-, s- or t-butyl,
$R^2$ represents methyl, ethyl, n- or i-propyl, n-, i-, s- or t-butyl, methoxycarbonyl or ethoxycarbonyl, or together with $R^1$ and the nitrogen atom to which they are attached represents optionally methyl- or ethyl-substituted pyrrolidine, piperidine or morpholine, Y represents the same grouping which is already attached to the sulphur atom, G represents oxygen or represents in each case optionally fluorine-, chlorine- or bromine-substituted dimethylene (ethane-1,2-diyl), ethene-1,2-diyl or one of the groupings below, in which in each case the left side is attached to Z:

—Q—CQ—, —CQ—Q—, —$CH_2$—Q—; —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^8$)=N—O—, —C($R^8$)=N—O—$CH_2$—, —N($R^9$)—, —CQ—N($R^9$)—, —N($R^9$)—CQ—, —Q—CQ—N($R^9$)—, —N=C($R^8$)—Q—$CH_2$—, —CH($R^8$)—O—N=CH—, —C($R^8$)=N—N=CH—, —N($R^9$)—CQ—Q—, —CQ—N($R^9$)—CQ—Q—, —N($R^9$)—CQ—Q—$CH_2$—, —Q—C($R^8$)=N—O—$CH_2$—, —N($R^9$)—C($R^8$)=N—O—$CH_2$—, —O—$CH_2$—C($R^8$)=N—O—$CH_2$—, —N=N—C($R^8$)=N—O—$CH_2$—, —C(=N—O—$R^{10}$)—C($R^8$)=N—O—$CH_2$—, —C(=N—O—$R^{10}$)—C($R^8$)—O—N=CH—, —C(=N—O—$R^{10}$)—C($R^8$)—N—

N=CH—, —C(=N—O—R$^{10}$)—C(R$^8$)—O—N=C(CH$_3$)—, —T—Ar$^1$— or —T—Ar$^1$—Q—,
where
n represents the number 0, 1 or 2,
Q represents oxygen or sulphur,
R$^8$ represents hydrogen, cyano, methyl, ethyl or cyclopropyl and
R$^9$ represents hydrogen, methyl, ethyl or cyclopropyl,
R$^{10}$ represents hydrogen, methyl, ethyl, n- or i-propyl, n-, i-, s- or t-butyl or represents optionally fluorine-, chlorine-, bromine-, cyano-, methyl-, ethyl-, n- or i-propyl, n-, i-, s- or t-butyl-, methoxy-, ethoxy-, n- or i-propoxy-, trifluoromethyl-, trifluoroethyl-, difluoromethoxy-, trifluoromethoxy-, difluorochloromethoxy- or trifluoroethoxy-substituted benzyl,
T represents a single bond, represents oxygen, sulphur, —CH$_2$O—, —CH$_2$—S— or represents optionally substituted alkanediyl,
Ar$^1$ represents phenylene or pyridinediyl, each of which is optionally mono- to trisubstituted by identical or different substituents, represents in each case optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, where the possible substituents are preferably selected from the list below:
fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and
L$^1$, L$^2$, L$^3$ and L$^4$ are identical or different and independently of one another each represent hydrogen, fluorine, chlorine, bromine, methyl or ethyl,
W represents hydrogen, fluorine, cyano or thiocyanato and
Z represents methyl, ethyl, n- or i-propyl, n-, i-, s- or t-butyl, allyl, 2-buten-1-yl, 2-(1-methyl)-propyl, 2-methyl-2-buten-1-yl, propargyl, tetrahydropyranyl, t-butyl substituted tetrazole or represents phenyl, 1,2,4-thiadiazolyl, 1,3,4-thiadiazolyl, 1,2,4-oxadiazolyl, 1,3,4-oxadiazolyl, pyridinyl, pyrimidyl, tetrahydrobenzofuranyl, pyridazinyl, pyrazinyl, 1,2,3-triazinyl, 1,2,4-triazinyl or 1,3,5-triazinyl, each of which is optionally mono- to trisubstituted by identical or different substituents, where the possible substituents are preferably selected from the list below:
amino, fluorine, chlorine, bromine, iodine, cyano, nitro, methyl, ethyl, formyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, phenyl;
in each case doubly attached methylenedioxy, ethylenedioxy, each of which is optionally mono- to tetrasubstituted by identical or different substituents from the group consisting of fluorine, chlorine, methyl, trifluoromethyl and ethyl,
or a grouping

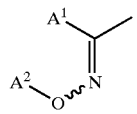

in which
A$^1$ represents methyl, ethyl, n- or i-propyl, n-, i-, s- or t-butyl, cyclopropyl or cyclobutyl and
A$^1$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

3. A compound of the formula (I) according to claim 1 in which
A represents hydrogen, ethoxycarbonyl, methyl, ethyl or cyclopropyl, or has the same meaning as R,
R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, 1,1-difluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N(R$^1$R$^2$),
in which
R$^1$ represents methyl, ethyl, n- or i-propyl, n-, i-, s- or t-butyl,
R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine,
Y represents the same grouping which is already attached to the sulphur atom,
G represents oxygen or, in particular, —O—CH$_2$—,
L$^1$, L$^2$, L$^3$ and L$^4$ each represent hydrogen,
W represents hydrogen, fluorine, cyano or thiocyanato and
Z represents methyl, ethyl, n- or i-propyl, n-, i-, s- or t-butyl, allyl, 2-buten-1-yl, 2-methyl-2-buten-1-yl, propargyl, tetrahydropyranyl or represents phenyl which is in each case optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, phenyl, in each case doubly attached methylenedioxy or ethylenedioxy, each of which is optionally mono- to tetrasubstituted by identical or different substituents from the group consisting of fluorine, chlorine, methyl, trifluoromethyl and ethyl, or a grouping

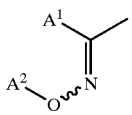

in which

A$^1$ represents methyl, ethyl, n- or i-propyl, n-, i-, s- or t-butyl, cyclopropyl or cyclobutyl and A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

4. A compound of the formula (I) according to claim 1 in which

A represents hydrogen, ethyl or methyl, or has the same meaning as R,

R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N(R$^1$R$^2$), in which R$^1$ represents methyl, ethyl, n- or i-propyl, n-, i-, s- or t-butyl, R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine, Y represents the same grouping which is already attached to the sulphur atom, G represents —C(R$^8$)=N—O—CH$_2$—, R$^8$ represents cyclopropyl or, in particular, methyl, L$^1$, L$^2$, L$^3$ and L$^4$ each represent hydrogen, W represents hydrogen, fluorine, cyano or thiocyanato and Z represents methyl, ethyl, n- or i-propyl, n-, i-, s- or t-butyl, allyl, 2-buten-1-yl, 2-methyl-2-buten-1-yl, propargyl or represents pyridyl, pyrimidyl or, in particular, phenyl, each of which is optionally mono- to trisubstituted by identical or different substituents where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy or ethylenedioxy, each of which is optionally mono- to tetrasubstituted by identical or different substituents from the group consisting of fluorine, chlorine, methyl, trifluoromethyl and ethyl.

5. A compound of the formula (I) according to claim 1 in which

A represents hydrogen, methyl or ethyl, or has the same meaning as R,

R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N(R$^1$R$^2$), in which R$^1$ represents methyl, ethyl, n- or i-propyl, n-, i-, s- or t-butyl, R$^2$ represents methyl, ethyl, n- or i-propyl, n-, i-, s- or t-butyl, methoxycarbonyl or ethoxycarbonyl, or together with R$^1$ and the nitrogen atom to which they are attached represents optionally methyl- or ethyl-substituted pyrrolidine, piperidine or morpholine, Y represents the same grouping which is already attached to the sulphur atom, G represents —T—Ar$^1$—O—, Ar$^1$ represents 1,2,4-thiadiazoldiyl, 1,3,4-thiadiazoldiyl, 1,2,4-oxadiazoldiyl, 1,3,4-oxadiazoldiyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy, difluorochloromethoxy, T represents a single bond, represents oxygen, sulphur, —CH$_2$O—, CH$_2$—S—, methylene, ethylene or propylene and $L^1$, $L^2$, $L^3$ and $L^4$ each represent hydrogen, W represents hydrogen, fluorine, cyano or thiocyanato and Z represents methyl, ethyl, n- or i-propyl, n-, i-, s- or t-butyl, allyl, 2-buten-1-yl, 2-(1-methyl)-propyl, 2-methyl-2-buten-1-yl, propargyl or represents pyridyl, pyrimidyl, thienyl, tetrahydrobenzofuranyl or, in particular, phenyl, each of which is optionally mono- to trisubstituted by identical or different substituents from the group consisting of amino, fluorine, chlorine, bromine, iodine, cyano, nitro, methyl, ethyl, formyl, n- or i-propyl, n-, i-, s- or t-butyl, trifluoromethyl, methoxy, t-butyl-substituted tetrazole, ethoxy, n- or i-propoxy, difluoromethoxy, difluorochloromethoxy, trifluoroethoxy, trifluoromethoxy, methoximinoethyl, ethoximinomethyl, methoximinoethyl, ethoximinoethyl and in each case doubly attached methylenedioxy or ethylenedioxy, each of which is optionally mono- to tetrasubstituted by identical or different substituents from the group consisting of fluorine, chlorine, methyl, trifluoromethyl and ethyl.

6. A compound of the formula (I) according to claim 1 in which

A represents hydrogen or methyl, or has the same meaning as R,

R represents methylthio, ethylthio, n- or i-propylthio, n-, i-, s- or t-butylthio, difluoromethylthio, trifluoromethylthio, difluorochloromethylthio, dichlorofluoromethylthio, trichloromethylthio, 2,2,2-trifluoroethylthio, methoxycarbonylthio, ethoxycarbonylthio, methylthiocarbonyl, ethylthiocarbonyl, n- or i-propylthiocarbonyl, represents phenylthio which is optionally mono- to trisubstituted by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, methoxycarbonyl or ethoxycarbonyl, represents —S—Y, —S—N($R^1R^2$), in which $R^1$ represents methyl, ethyl, n- or i-propyl, n-, i-, s- or t-butyl, $R^2$ represents methyl, ethyl, n- or i-propyl, n-, i-, s- or t-butyl, methoxycarbonyl or ethoxycarbonyl, or together with $R^1$ and the nitrogen atom to which they are attached represents optionally methyl- or ethyl-substituted pyrrolidine, piperidine or morpholine, Y represents the same grouping which is already attached to the sulphur atom, G represents —C(=N—O—$R^{10}$)—C($R^8$)=N—O—$CH_2$— in which $R^8$ represents methyl or cyclopropyl and $R^{10}$ represents hydrogen, methyl, ethyl, n- or i-propyl, n-, i-, s- or t-butyl or represents optionally fluorine-, chlorine-, bromine-, cyano-, methyl-, ethyl-, n- or i-propyl-, n-, i-, s- or t-butyl-, methoxy-, ethoxy-, n- or i-propoxy-, trifluoromethyl-, trifluoroethyl-, difluoromethoxy-, trifluoromethoxy-, difluorochloromethoxy- or trifluoroethoxy-substituted benzyl, $L^1$, $L^2$, $L^3$ and $L^4$ each represent hydrogen, W represents hydrogen, fluorine, cyano or thiocyanato and Z represents methyl, ethyl, n- or i-propyl, n-, i-, s- or t-butyl, allyl, 2-buten-1-yl, 2-methyl-2-buten-1-yl or represents pyridyl, pyrimidyl or, in particular, phenyl, each of which is optionally mono- to trisubstituted by identical or different substituents, where the possible substituents are preferably selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy, ethylenedioxy, each of which is optionally mono- to tetrasubstituted by identical or different substituents from the group consisting of fluorine, chlorine, methyl, trifluoromethyl and ethyl, or t-butyl-substituted tetrazole.

7. A compound of the formula (I) according to claim 1 in which

G represents oxygen or one of the groupings below in which in each case the left side is attached to Z:
—Q—$CH_2$—, —C($R^8$)=N—O—$CH_2$—, —N=C($R^8$)—Q—$CH_2$—, —CH($R^8$)—O—N=CH—, —C($R^8$)=N—N=CH—, —C(=N—O—$R^{10}$)—C($R^8$)=N—O—$CH_2$—, —C(=N—O—$R^{10}$)—C($R^8$)—O—N=CH—, —C(=N—O—$R^{10}$)—C($R^8$)—N—N=CH— or —T—$Ar^1$—Q— where $R^8$, $R^9$, $R^{10}$, T, $Ar^1$ and Q are as defined in claim 1.

8. A compound of the formula (I) according to claim 1 in which

A represents methyl.

9. A compound of the formula (I) according to claim 1 in which

G represents oxygen, —O—$CH_2$—, —C($CH_2$)=N—O—$CH_2$— or optionally fluorine-substituted pyrimidinyloxy.

10. A compound of the formula (I) according to claim 1 in which

Z represents unsubstituted or mono- or disubstituted phenyl.

11. A process for preparing a compound of the formula (I) as defined in claim 1, characterized in that amides of the formula (II)

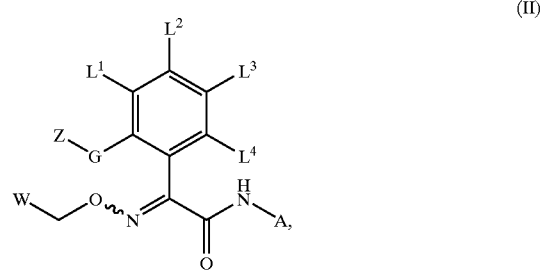

(II)

in which

A, G, $L^1$, $L^2$, $L^3$, $L^4$ and Z are each as defined in claim 2, are reacted with an electrophilic reagent of the formula (III)

R—X (III)

in which

R is as defined in claim 2 and

X represents a leaving group, if appropriate in the presence of a diluent and if appropriate in the presence of a base.

12. A microbicidal composition comprising a microbicidally effective amount one or more of the compounds of claim 1 and a member selected from the group consisting of extenders, carriers, surfactants and mixtures thereof.

13. A method for controlling undesirable microorganisms comprising allowing a microbicidally effective amount of one or more of the compounds of claim 1 to act on said microorganisms and/or their habitat.

14. A process for preparing a microbicidal composition comprising mixing one or more of the compounds of claim 1 with a member selected from the group consisting of extenders, carriers, surfactants and mixtures thereof.

\* \* \* \* \*